United States Patent
Forth

[19]

[11] Patent Number: 5,846,816
[45] Date of Patent: Dec. 8, 1998

[54] APPARATUS FOR BIOMASS PRODUCTION

[75] Inventor: Kevin Forth, Parkerville, Australia

[73] Assignee: Enviro Research Pty Ltd., West Perth, Australia

[21] Appl. No.: 860,818

[22] PCT Filed: Dec. 20, 1995

[86] PCT No.: PCT/AU95/00870

§ 371 Date: Jul. 10, 1997

§ 102(e) Date: Jul. 10, 1997

[87] PCT Pub. No.: WO96/21723

PCT Pub. Date: Jul. 18, 1996

[30] Foreign Application Priority Data

Jan. 13, 1995 [AU] Australia ................. PN0600

[51] Int. Cl.$^6$ .................................... C12M 3/00
[52] U.S. Cl. .................. 435/292.1; 435/286.7; 435/296.1; 435/304.1
[58] Field of Search .............. 435/286.7, 289.1, 435/292.1, 296.1, 304.1; 366/101, 107, 165.2

[56] References Cited

U.S. PATENT DOCUMENTS

| 4,205,133 | 5/1980 | Wick ........................................ 435/287 |
| 5,151,347 | 9/1992 | Delente et al. ............................. 435/3 |
| 5,162,051 | 11/1992 | Hoeksema ................................... 47/1.4 |
| 5,320,963 | 6/1994 | Knaack et al. ........................... 435/286 |
| 5,447,629 | 9/1995 | Chaumont et al. ..................... 210/96.1 |

FOREIGN PATENT DOCUMENTS

| 261872 | 3/1988 | European Pat. Off. ......... C12M 1/00 |
| 5-146287 | 6/1993 | Japan .................................. 435/292.1 |
| WO 91/08314 | 6/1991 | WIPO ............................. C12Q 3/00 |
| WO 95/19424 | 7/1995 | WIPO ............................. C12M 3/02 |

*Primary Examiner*—David A. Redding
*Attorney, Agent, or Firm*—Needle & Rosenberg, P.C.

[57] ABSTRACT

A bioreactor for biomass production having (i) a substantially transparent chamber, the chamber being suitable for containing biomass in a liquid phase, and having a base portion, an upper portion and a number of sidewalls between the base portion and the upper portion, the sidewalls being configured so as to diverge from the base portion towards the upper portion; and (ii) a circulating means for circulating the contents of the chamber to create a motive force in the liquid phase to ensure continual mixing of all of the biomass and a semi-continuous exposure of the biomass to a light source.

31 Claims, 7 Drawing Sheets

APPARATUS FOR BIOMASS PRODUCTION

THIS INVENTION relates to an apparatus for the production of biomass and is particularly concerned with a process for cultivating biomass using the apparatus.

The long term potential for using autotrophic organisms in the generation, treatment and accumulation of commercial products and wastes has become increasingly apparent in recent years. Autotroph's are organisms that utilise $CO_2$ as their major source of carbon and obtain energy from the sun through photosynthesis (photoautotrophs) or from organic or inorganic reduced chemicals (chemoautotrophs). Typical examples of which include plants, seaweed, algal cultures (eg. Chlorella, Spirolina, Dunaliella etc), bacteriophages, photosynthetic bacteria and the like. Due to these modest requirements autotrophic organisms are eminently suited for producing biomass. Algal cultures, for example, have been grown for food for animals and humans, for the treatment of sewerage and waste, for the accumulation of radioactive waste, for the propagation of enzymes and other products having industrial and research application and for the production of oils and other nutrients having nutritional value.

Traditional procedures employed for culturing autotrophic organisms have involved the use of shallow open ponds or open channels exposed to sunlight. These relatively crude methods of culturing autotrophic organisms have proved impractical in that they are subject to contamination by dust, microorganisms, insects, other animals, and environmental pollutants and have limited capacity to control the degree of exposure to light, temperature, respiration and other factors.

One attempt to overcome these problems has involved the use of a bioreactor system having a light admitting pipe of comparatively small diameter wound substantially horizontally against the face of a series of flat vertical panels. The problems associated with this form of bioreactor include low density of biomass in the liquid within the tubes, low penetration of light, coating of the tubes with autotrophic organisms due to low velocity flow there through thus reducing transparency, overheating in summer weather, high land usage and process control problems of manipulating sufficiently large numbers of such units for commercial production. Further, the design of this bioreactor gives it an inherently unstable construction unable to withstand adverse weather conditions.

An alternative construction has comprised an upstanding core structure around which is wound a substantially transparent tube which allows at least 90% transmission of light so that, in use, the exterior of the wound tube is exposed to natural light. To encourage penetration of light into the tube, the upstanding core structure is fitted with a light reflecting means. Through the wound tube there is passed a synthesis mixture comprising living plant material such as algae, bacteriophages and seaweed together with essential nutrients for growth. Again, coating of the tubes with autotrophic organisms, overheating in summer weather, the overall construction costs, the limited volume of liquid that can pass through the tubes at any one time and the difficulty of sterilising the apparatus between culture batches present inherent disadvantages to the use of such bioreactors.

A somewhat more sophisticated construction has comprised a bioreactor for the cultivation of photosynthetic microorganisms in which there is a plurality of baffles mounted in a photobioreactor tank where in the baffles form hollow cavities through the bioreactor which enable the insertion of light sources through openings in the tank wall. Although this construction can maintain a higher density of biomass in culture liquid and reduces land usage, the complexity of the bioreactor tank, the overall construction costs and overheating in summer weather makes this tank uneconomical to use on a commercial scale. Further it is particularly difficult to clean and sterilise between operation cycles.

The present invention seeks to provide an improved bioreactor which at least can be manufactured in a variety of different sizes and lengths, and which is suitable for the commercial production of autotrophic organisms.

Thus, the present invention resides in a bioreactor for biomass production comprising:

(i) a substantially transparent chamber, the chamber being at least suitable for containing biomass in a liquid phase, and having a base portion, an upper portion and a number of side walls between the base portion and the upper portion, the side walls being configured so as to generally diverge from the base portion towards the upper portion; and (ii) a circulating means for circulating the contents of the chamber, wherein the circulating means creates a suitable motive force within the liquid phase to ensure continual mixing of substantially all of the biomass and at least semi-continuous exposure of biomass to a light source.

There are a number of parameters that affect the production of biomass within the bioreactor according to the invention. Two of these parameters are the amount of light penetrating the chamber and the speed with which biomass is circulated within the chamber.

Preferably, the substantially transparent nature of the chamber allows light to pass into it. As the density of the biomass in the bioreactor increases, the intensity of light penetration into the liquid phase will most likely decrease. Preferably, substantially all of the biomass is exposed to the light at least on a semi continuous basis. In some circumstances the biomass may be subjected to continual exposure to the light source. This light source may be natural light such as sunlight or may be artificially generated.

The circulation rate within the chamber should be set at a suitable level to ensure that continual mixing of substantially all of the liquid phase is achieved and so that the biomass is exposed to light during circulation without unduly stressing the biomass. It will be appreciated that some variation in the configuration of the present invention may be achieved without departing from he invention. Generally the circulation system employed in the invention will keep substantially all of the biomass in continual suspension and will prevent settling of that biomass in the bioreactor. Preferably, all of the biomass is maintained in continual suspension.

The motive force required to generate a suitable circulation rate of the liquid phase within the bioreactor will vary depending on the size of the bioreactor, the biomass cultivated in the reactor and the density of that biomass. The minimum circulation rate of the biomass in the bioreactor is preferably greater than a rate that would lead to settling of that biomass. The maximum circulation rate is desirably less than a rate that would lead to excessive foam development on the surface of the liquid phase in the bioreactor and or that would lead to the biomass being subjected to excessive environmental stress. Preferably the circulation rate is set between the minimum circulation rate and the maximum circulation rate. More preferable the circulation rate is set near to the minimum circulation rate. For example, in an elongate 350 litre trough-like prism bioreactor with an inverted generally triangular cross-section, circulation can be generated by the release of a gas at or near the inverted apex of the bioreactor. The minimum gas input is preferably 12 litres per meter per minute. The maximum gas input is preferably 100 litres per meter per minute. In a highly preferred form of the invention the gas input is 20 litres per meter per minute.

Since the dynamics of the environment in the bioreactor will continually undergo change as the concentration of biomass increases, the circulation rate is preferable monitored and adjusted so that the circulation rate never falls below the minimum circulation rate.

It will be appreciated that the present invention may be used to produce biomass of various types and forms or products derived from the biomass. The term "biomass" as used herein includes all organisms capable of photosynthetic growth such as plant cells and microorganisms (including algae and euglena) in unicellular or multicellular form that are capable of growth in a liquid phase. The term may also include organisms modified artificially or by gene manipulation. The bioreactor of the present invention is particularly suited for cultivation of algae or photosynthetic bacteria. For example, the bioreactor may be used as a photobioreactor for the production of algal biomass. In this respect, algae of various types (eg. Chlorella, Spirolina, Dunaliella etc), which have particular and diverse growth requirements may be cultivated in the bioreactor.

In order for the biomass to respire there needs to be provided in the liquid phase one or more means for introducing a gas phase into the liquid phase. This may be achieved by any chemical means which does not kill the biomass or by one or more conduits which open into the bioreactor. Any gas that is required for photosynthetic activity should be introduced into the bioreactor by this delivery means. Preferably the gas is air or a mixture of carbon dioxide and oxygen. To avoid contamination of the biomass in the reactor the introduced gas is preferable sterilised before release into the reactor to remove contaminating pathogens. In a highly preferred form of the invention circulation of the liquid phase is achieved using the gas delivery system.

It will be appreciated that the circulation means may be of various forms, depending on the configuration of the chamber, provided that it at least acts to circulate the contents of the chamber and is capable of providing aeration to the liquid phase held within the chamber. Moreover the circulation means may be located anywhere within the bioreactor provided it is capable of creating a suitable motive force within the liquid phase to ensure continual mixing of substantially all of the biomass and at least semi-continuous exposure of the biomass to a light source.

Preferably the circulation means is located adjacent to the base portion or above the base portion near the top of the bioreactor. For example, when the circulation means is located adjacent to the base portion within the bioreactor it desirably generates an upward movement of biomass and liquid phase from the base portion to the top of the bioreactor. The upward movement of liquid phase and biomass impacts the top surface of the vessel ensuring brief guaranteed light exposure for most of the biomass in the liquid phase. Following contact with the top surface of the bioreactor the liquid phase containing biomass moves outwards towards the sides of the bioreactor. This movement also ensures exposure of the biomass within the liquid phase to light. The liquid phase containing biomass then moves down the sides of the bioreactor towards the base portion, from where it is again caught by the circulation means and driven upwards towards the top of the bioreactor. This mixing regime facilitates rapid and consistent photosynthetic growth of the biomass because it ensures effective exposure of substantially all biomass in the liquid phase to the light and also engenders a regular 'flashing' light pattern that has been shown to enhance growth of some photosynthetic organisms.

Preferably the bioreactor has a high surface area to volume ratio. This may be achieved by employing almost the entire surface of the bioreactor as a active light absorbing/transmitting surface. Light absorption and transmission may be further enhanced by employing transparent structural material in the construction of the bioreactor and by suspending the bioreactor slightly off a reflective base surface.

Preferably, the bioreactor is formed as an elongate trough-like prism, the prism having an inverted generally triangular cross-section. The sides of the generally triangular cross-section are preferably approximately equal and the inverted apex defines the base portion of the chamber. Further, the circulating means is preferably provided within the chamber at or near the inverted apex, and the sides of the prism define the side walls and cover means of the chamber.

When the bioreactor is formed as an elongate trough-like prism, longitudinal motion of the liquid phase may be introduced into circulation by removal of liquid phase from one end of the bioreactor and its subsequent return to the other end as part of a biomass management procedure. Such movement would also serve to prevent localised entrainment of biomass that may occur which may deleteriously affect light exposure regimes of the bioreactor. Transfer of the liquid phase in this manner also allows for complete mixing and transmission of chemical and physical manipulation of the biomass liquid phase environment.

The circulation means may be provided as a conduit extending through the length of the chamber which is located at or near the base portion of the chamber, the conduit being perforated and connected to a gas source such that in operation the passage of gas out of the conduit and into the chamber causes circulation of the chamber contents. The passage of gas from the conduit through the liquid phase also provides a means for gas diffusion into the liquid phase, thus aerating that phase. In this preferred form the gas is preferably sterile air. In a highly preferred form the perforations are disposed towards the underside of the conduit, the downward passage of gas assisting in preventing particulate material in the chamber from settling below the conduit.

Thus, in a preferred form the present invention resides in a bioreactor for biomass production comprising:

(i) a substantially transparent chamber, the chamber being at least suitable for containing biomass in a liquid phase, and having a narrow base portion, an upper portion capable of being sealed by a cover means and a number of side walls diverging from the base portion to the upper portion; and (ii) a circulating means for circulating the contents of the chamber, wherein the circulating means creates a suitable motive force to ensure continual mixing of the liquid phase and exposure of biomass to the light wherein the circulating means is located at or near the lower most portion of the base portion and comprises a conduit extending through the length of the bioreactor, the conduit being perforated and connected to a gas source wherein the perforations in the conduit are disposed towards the underside of the conduit, such that in operation the downward passage of gas out of the conduit and into the liquid phase (a) prevents particulate material in the chamber from settling below the conduit, (b) causes circulation of the liquid phase; and (c) allows gas diffusion into the liquid phase.

The chamber may be formed as separate pieces of substantially transparent material joined together to form the base portion, side walls and cover means. However, in a preferred form the base portion, side walls and cover means are provided as an integral unit, the intersection of the parts preferably being formed as rounded edges. In a high preferred configuration the bioreactor is specifically designed as an elongate triangular structure, which can accommodate large volumes of liquid phase.

The cover means is preferably provided with a slight arch resulting in a cover means with a generally convex upper surface. In this form vents are preferably provided and positioned towards the middle of the convex upper surface such that gas is vented from the chamber. The vents may include a filter means, the filter means at least being suitable for preventing particulate material from entering the chamber. Further the vents may also serve as sample points for sampling biomass from within the chamber of the bioreactor.

While the vents may vent directly to the atmosphere they may also be connected to a manifold which in turn is connected to an oxygen separating and venting system. Thus expelled gasses containing unused carbon dioxide may be collected from the vents and scrubbed of their oxygen content before being returned to the bioreactor, in order to facilitate conservation and efficient use of the carbondioxide.

Preferably, the bioreactor also includes a temperature control means for controlling the temperature of the liquid phase. In one form, the temperature control means may comprise one or more heat exchange conduits forming a fluid path or paths for the circulation of heat exchange medium within the chamber.

To further regulate the circulation of the contents of the chamber, the circulation means may further comprise baffles. The baffles may be located within the chamber and may be positioned in a fashion to further enhance the circulation of the contents of the chamber.

In one especially preferred form the temperature control means may be of a suitable form that the baffles (when present) may be integrally formed with the temperature control means or alternatively the temperature control means may perform a dual role of regulating temperature within the chamber and providing the baffle means.

The bioreactor may also include a pH control means for controlling the pH of the liquid phase. The pH control means preferably comprises a pH probe located in the liquid phase, the probe being operatively connected to a supply of $CO_2$. The pH of the liquid phase may then be adjusted by controlling the delivery of $CO_2$, or by addition of other chemicals.

In some situations the natural diffusion of light into the chamber may be less than optimum and in these situations it may be beneficial to enhance the distribution of light within the chamber. In this respect the bioreactor is preferably located on a light reflective base, the base ensuring that light delivered to the chamber from an external source is maximised.

Additionally or in the alternative the bioreactor may comprise one or more light conduction means which promote effective distribution of light in the bioreactor. The light conduction means may be located within the bioreactor or external to the bioreactor. If the light source is located within the bioreactor it may be suspended above the liquid phase of submerged within the liquid phase. If the light source is located external to the bioreactor it may be positioned anywhere around it. Preferably the light source is located beneath the side walls of the bioreactor. In a highly preferred form of the invention the bioreactor may be suspended or positioned within a light box wherein the light source is angled substantially perpendicular to the sides of the vessel In a preferred embodiment of the invention the bioreactor may also include one or more jacketing means which are capable of at least partially covering the external surface of the bioreactor. When present, the jacketing means may provide an additional means for insulating the bioreactor. While any means known in the art may be used to support the jacket around the external surface of the bioreactor, the jacket is preferably mounted to the outer wall of the reactor via a skeleton or lattice arrangement that is fixed to the chamber. The skeleton or lattice may be made of any material such as wood, metal or plastic and is preferably constructed with large apertures therein which permit penetration of light into the bioreactor chamber.

Although the jacketing means may be formed of any material that is suitable for insulating the chamber preferably it is made of a transparent material which permits the entry of light into the bioreactor. It will be appreciated that the jacketing means may provide a means for externally heating or cooling the bioreactor. In this instance the jacketing means is preferably attached to the skeleton or lattice arrangement, to the outer wall of the bioreactor and to the bioreactor base. Preferably the jacketing means is sealed such that it is capable of holding a heat exchange medium. For example the jacketing means may comprise a transparent flexible polyethylene or polyvinyl chloride film which is in sealing engagement with an outer frame skeleton which may be attached to the bioreactor. Hot or cold air can then be circulated between the jacketing means and the external surface of the bioreactor by one or more pump means. Said pump means being preferably connected to one or more control means which are capable of monitoring the internal temperature of the bioreactor and adjusting the temperature of the circulating air to maintain a constant temperature inside the chamber. This control means might also be connected to the heat exchanger.

In addition to, or as an alternative to the jacketing means there may be provided on the external surface of the bioreactor a light control means which is capable of adjusting the amount of light entering the chamber. While any means known in the art may be employed for this purpose the light control means preferably consists in a series of blinds which may be open or closed to vary the amount of light entering the chamber. More preferably said light control means is connected to one or more light measuring means. When the amount of light measured by this means exceeds a preset reference value the control means will for example close the light control means for a defined period of time, after which it will reopen the light control means.

The bioreactor may also be in fluid communication with a separate vessel containing liquid phase. The separate vessel may act as a reservoir, increasing the volume of the system. It may act as a dark phase area, during high light intensities and growth conditions. Alternatively it may act as a settling system from which biomass may be removed from the bioreactor. When used in this manner the bioreactor may be connected to existing technologies to control the flow rate of the liquid phase into the settling vessel to enhance settling of the biomass in the settling vessel. The biomass can then be removed continuously or intermittently, with the settled material being collected and processed. This procedure may serve as a harvest system for removing biomass from the system and maintaining optimal cell densities within the liquid phase The bioreactor may also be used in various locations which experience a variety of climatic conditions. The internal environment of the vessel and the conditions experienced by the biomass therein are preferably kept constant and optimal for cell growth, survival or for the induction of specific biochemical processes with in the cultures. This may be achieved using a closed system bioreactor wherein undesirable organisms can be excluded and the physicochemical environment of the liquid phase within the bioreactor can be artificially controlled.

Control of the physico-chemical conditions within the bioreactor can be achieved using standard computer controls and electronic sensors. Chemicals for nutrient level maintenance and for control of pH and other factors can be added automatically directly into the liquid phase within the bioreactor. The computer controls may also control the temperature of the liquid phase in the vessel by either controlling a heat exchanger system within the bioreactor or by removing culture from the main vessel and passing it through a simple heat exchanger in, for example, a temperature controlled water bath.

Removal and passaging of liquid phase containing biomass from the bioreactor to another vessel containing a gas delivery system and back to the bioreactor may be used to increase the concentration of dissolved carbon dioxide in the liquid phase. In this form the biomass may be diverted through an entrained bubble contactor, or other means for dissolving carbon dioxide or other gases into the liquid phase without losses to the environment or stressing of the biomass in the bioreactor.

Removal and passaging of liquid phase may also be used to control the temperature of the liquid phase. In this form the liquid phase is passed through a vessel containing at least a temperature control means which is capable of varying the temperature of the liquid phase, before being returned to the bioreactor.

The present invention may consist as either a single bioreactor chamber or as a multiple of chambers all of which are interconnected. If multiple chambers are provided then one or more of the chambers may be cloaked in darkness to assist in manipulation and control of dark phase growth and respiration. In this instance, the flow of liquid phase between the chambers is preferably controlled by a computer means which is capable of monitoring the cell density within each chamber and which is capable of transferring liquid phase (including biomass) between the chambers in response to changes in cell density.

It will be understood that bioreactors of the type described herein may be used on a batch basis wherein a single culture of biomass can be grown in the bioreactor at any one time, or they can be used in a continuous production cycle wherein there is a steady feed of essential nutrients and liquid phase into the bioreactor as well as a continuous discharge of liquid phase containing cultured biomass from the bioreactor.

In a single batch operation, the nutrients may be added to the bioreactor chamber, mixed well with a solution containing biomass, and then left alone for a period of time until the required density of biomass is achieved. The resultant mixture can then be removed from the bioreactor for processing. Notably this form of operation leads to a relatively unsteady environmental state within the bioreactor chamber because the nutrient concentration and cell density vary with time.

As an alternative, during an operating sequence whose duration may depend on the nature and intensity of the light irradiation, the concentration of the nutrient solution and the biomass in the liquid phase, biomass growth rates may be maintained by adding essential nutrients to the liquid phase. Preferably essential nutrients for growth and propagation of the biomass are added to the bioreactor chamber as they are consumed by the biomass.

To effectively monitor changes in such nutrients there is preferably present into the bioreactor chamber one or more measuring means which are capable of detecting variations in nutrient levels. More preferably the measuring means are connected to a computer control means which is capable of monitoring nutrient levels in the liquid phase and when necessary capable of introducing nutrients into the bioreactor chamber.

If a large volume of biomass is required (ie. for commercial production of biomass) the bioreactor chamber is preferably operated in a continuous production cycle wherein there is a steady feed of new nutrients into the chamber as well as a steady discharge of biomass. If multiple bioreactors are connected in series the first bioreactor may be provided with a steady feed of new reactants. A continuous flow of the reacting materials may then pass from one bioreactor to the next. The cultured biomass may then be continuously discharged from the last of the series of bioreactors. In certain circumstances it may be useful to introduce additional nutrients or other compounds to various bioreactors in the sequence (ie where a bioreactor becomes depleted of such nutrients or other compounds). Complete mixing of the contents of the liquid phase in the bioreactor means that a constant biomass concentration for biomass entering and leaving each bioreactor can be maintained. This may result in a change in the concentration of biomass from one bioreactor to the next. Preferably the concentration of biomass increases as it passed through the series of bioreactors.

One advantage of using a plurality of bioreactors in continuous series to produce biomass, apart from the simplicity of construction, is the ease of temperature and pH control. The material entering a given vessel plunges immediately into a large volume of biomass and because of agitation, local variations in temperature and pH are minimal.

The present invention will now be described in more detail by way of example with reference to the accompanying drawings wherein.

Figure 1:
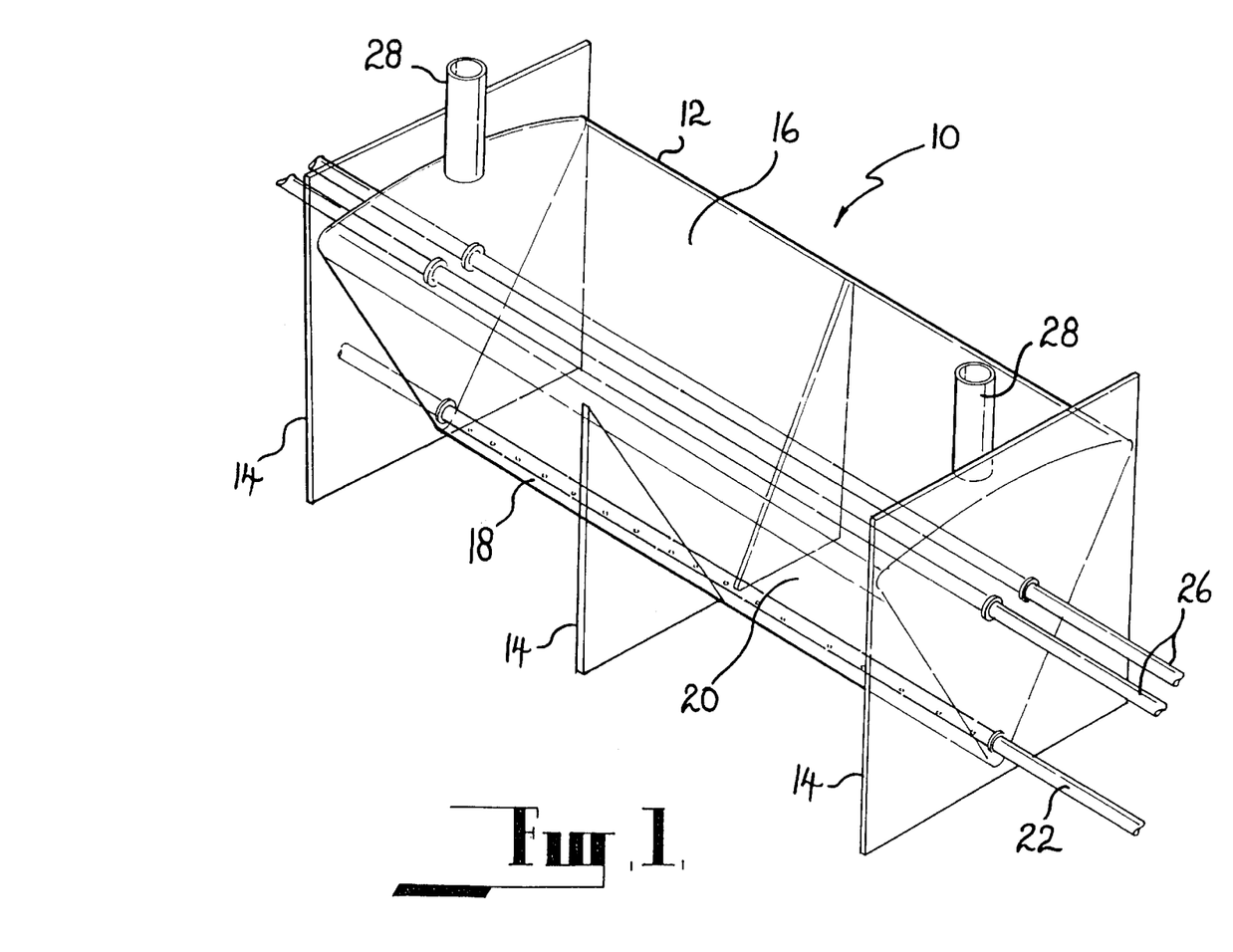
FIG. 1 is a perspective view from above of a bioreactor in accordance with a preferred embodiment of the invention.
Figure 3:
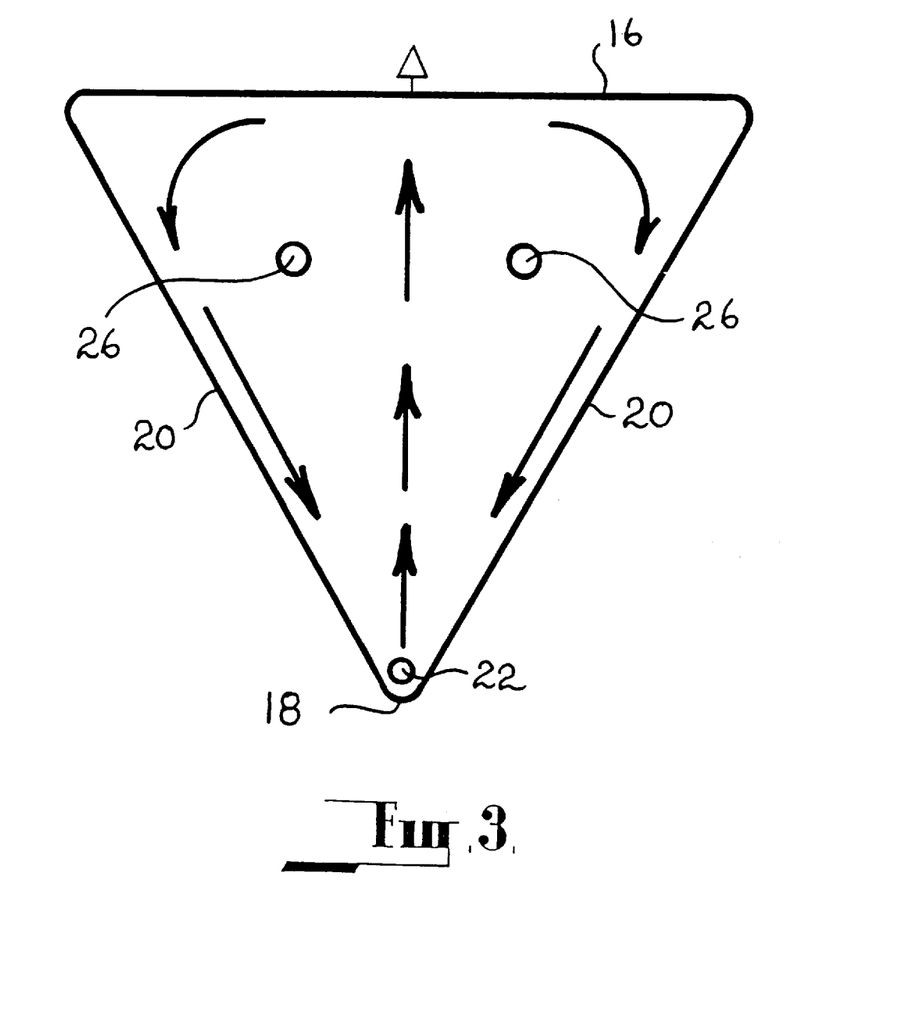
FIG. 3 is a simplified end view of the bioreactor of FIG. 1 with arrows indicating the liquid phase flow pattern within the chamber.

The bioreactor as shown in FIGS. 1 and 3 and generally indicated by the numeral 10 comprises a chamber 12 supported by three vertical support members 14, two of which are located at each end of the chamber and the third of which is located towards the middle of the chamber 12.

The chamber 12 is of an inverted generally triangular cross section and has a slightly convex cover means 16 closing the upper portion of the chamber 12. The chamber 12 further comprises a narrow base portion 18 and a pair of side walls 20.

A circulating means in the form of a conduit 22 is located within the chamber towards the base portion 18 of the chamber 12. The conduit 22 bears a plurality of perforations 24 along the length of its underside such that gas introduced into the chamber through the conduit passes out of the perforations in a substantially downward direction, thus preventing the settling of particulate material beneath the conduit 22. The conduit 22 of the embodiment extends through the chamber and has portions extending from either end to allow for a number of bioreactors to be connected in series.

Temperature control means in the form of a pair of conduits 26 are located towards the middle of the chamber 12 and extend the length of the chamber 12. The conduits 26 are connected to an external supply of heat exchange medium (not shown). Thus through the use of a thermostat and regulation of the temperature of the heat exchange medium, the temperature of the liquid phase within the chamber may be regulated and controlled to any predetermined setting.

The cover means 16 provides a pair of vents 28. The vents 28 being located at each end of the cover means 16 and being positioned towards the centre of the cover means 16 so as to be adjacent the highest part of the convex surface of the cover means 16. In operation there exists a positive pressure within the air vents 28 such that there is flow of excess gases out of the vents and negligible flow through the vents into the chamber thus preventing airborne contamination gaining access into the chamber via the vents 28.

Figure 2:
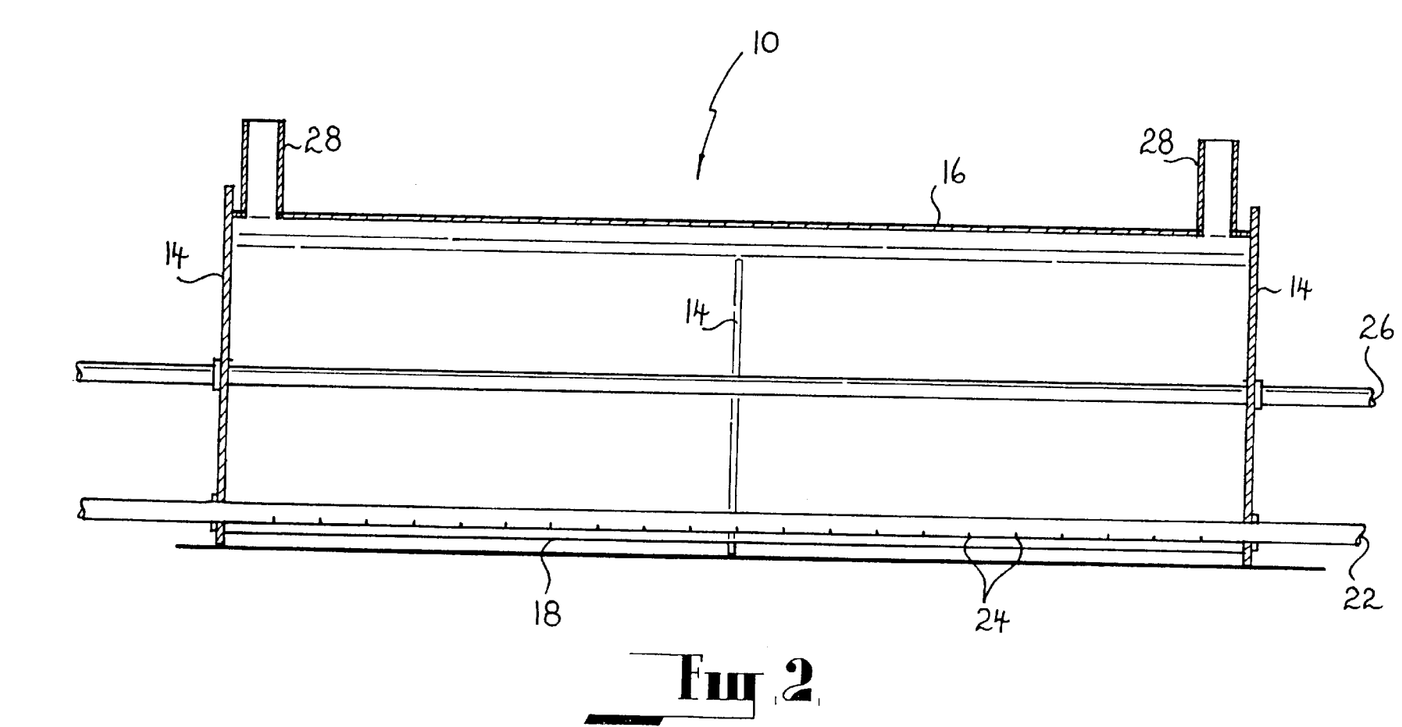
FIG. 2 is a longitudinal cross section of the bioreactor of FIG. 1.

In operation the bioreactor according to FIGS. 1 to 3 has a distinctive flow pattern of the liquid phase within the chamber 12. The flow pattern being specifically shown in FIG. 3. Air entering the chamber through the conduit 22 is directed down towards the lower part of the base portion 18 and then proceeds to travel vertically through the chamber 12 until it meets the underside of the cover means 16. Upon contact with the cover means, the air is urged towards the side walls 20. Excess air leaves the chamber through the vents 28. The passage of the air and its interaction with the liquid phase and the internal walls of the chamber 12 cause the liquid phase to circulate according to the arrows detailed in FIG. 3. Currents are set up in the liquid phase which act to circulate the liquid phase containing the biomass vertically up through the central region of the chamber 12, across the upper portion of the chamber directly below the cover means 16 and down the chamber directly adjacent the side walls 20 to the conduit 22 and the cycle is repeated.

Further, the passage of the liquid phase in the chamber 16 also serves to maintain the clarity of the side walls 20 and cover means 16 of the chamber 12. The liquid phase flow and the slope of the chamber walls prevents biomass settling on the walls and the directed movement of the liquid phase reduces the tendency of certain types of biomass such as algae to adhere to the walls of the chamber.

The flow of the liquid phase and configuration of the chamber 12 also result in the cover means 16 of the chamber 12 coming into contact with the liquid phase, this prevent condensation forming on the cover means 16. When the biomass contains photoautotrophs the cover means 16 represents a dominant photosynthetic surface, condensation on the cover means 16 may result in a loss of photosynthetically active radiation.

It will be seen that this circulation pattern results in the biomass within the chamber being regularly positioned adjacent the cover means 16 and the side walls 20 thus presenting the biomass to light entering into the chamber. In this respect it will be noted that whilst cell density of the biomass within the chamber is relatively low, the penetration of light into the chamber will be relatively high. The penetration of light into the chamber reducing significantly as the biomass increases in cell density.

In order to maximise the efficiency of light harvesting, the bioreactor may be oriented in a north-south direction, with appropriate corrections made for the latitude of the site, according to guidelines established for solar energy harvesting technologies. Within this basic north-south orientation the bioreactors may be set up in parallel and at a distance apart which corresponds to twice the triangular dimension of the vessel. This arrangement facilitates maximal efficiency of the light harvesting by the bioreactor and use of land; it is based on the maximal efficiency of 8 hours direct sunlight, out of a 12 hour day, without any shadowing effects from neighbouring tanks.

The bioreactor may be designed to be cleaned and disinfected in situ. Preferably the construction of the bioreactor will reflect established food industry procedures, which use food grade materials and also facilitate effective cleaning and disinfection of the vessel and all the associated infrastructure.

Preferably all inputs into the chamber are sterilised. Air is filtered to 0.2 $\mu$m and also treated with ultraviolet light at the point of supply to the bioreactor. Water and nutrient media added to the chamber may be filtered to 0.2–1.0 $\mu$m and also treated with UV radiation.

Inoculum for the vessel is preferably be grown under hygienic conditions and added to the bioreactor under hygienic conditions.

Within the chamber the density of the culture may be manipulated to maintain culture density for continuous or semi-continuous harvest regimes or else to facilitate batch harvest systems. Choice of harvest system and regime depends at least on the nature of the production system, biomass used and end use of the harvested product.

Elongate triangular bioreactors, substantially longer than the dimensions of the cross-sectional area have been tested. It has been found that biomass growth rates are relatively unaffected by the length of the bioreactor. Rather the cross-sectional triangular dimensions appear to be the most important predictor of growth rate. Thus the present invention can be scaled up to very large volumes without significant changes in the growth rate of the biomass.

Figure 4:
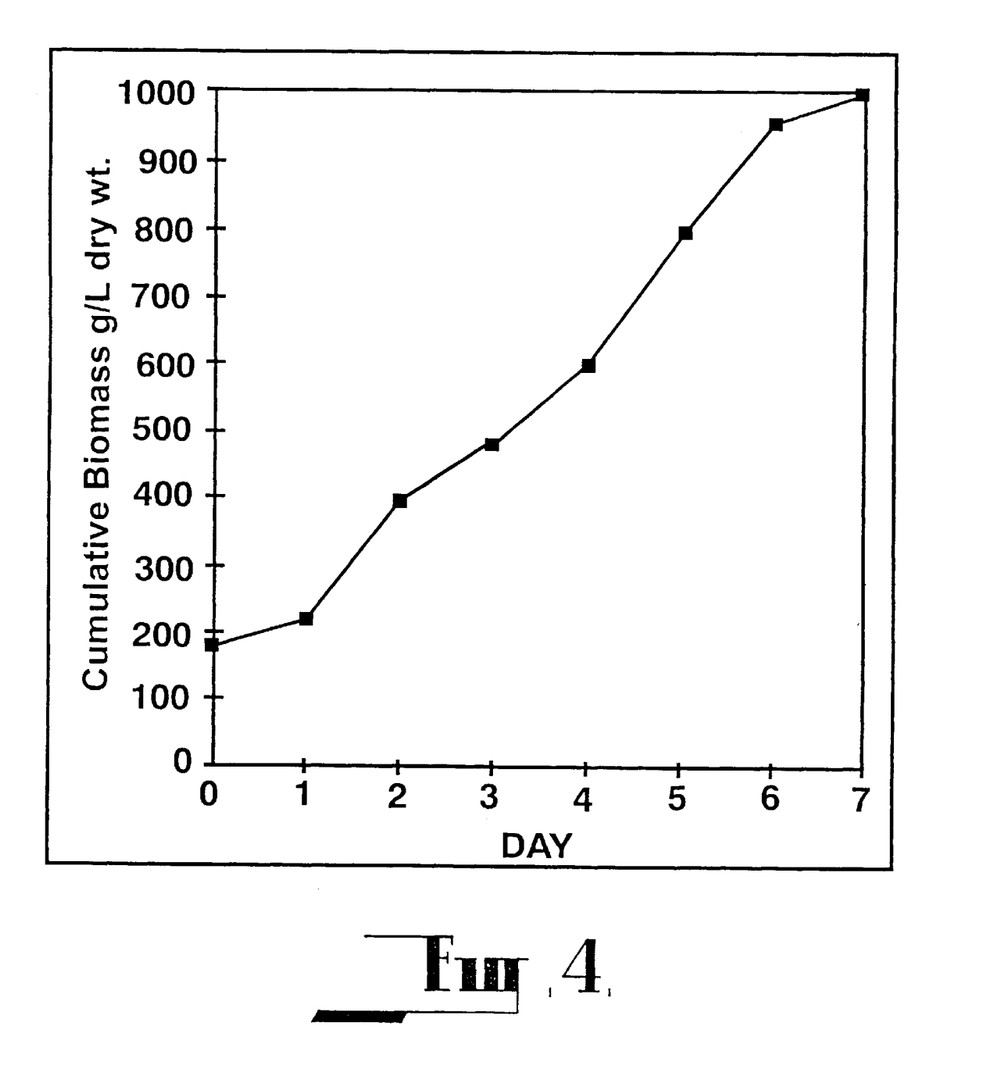
FIG. 4 is a graph of biomass v's time obtained using averaged results from two separate bioreactors of similar form to the bioreactor of FIG. 1, the bioreactors each having a capacity of 750 litres with triangular dimension of 1200 mm and length of 1200 mm.

FIG. 4 shows biomass increase over time in a 750 litre capacity bioreactor bearing a triangular cross section of equal side lengths of 1200 mm. The 750 litre bioreactor yielded 1000 mg of biomass per litre in 6 days under natural daylight conditions.

Figure 5:
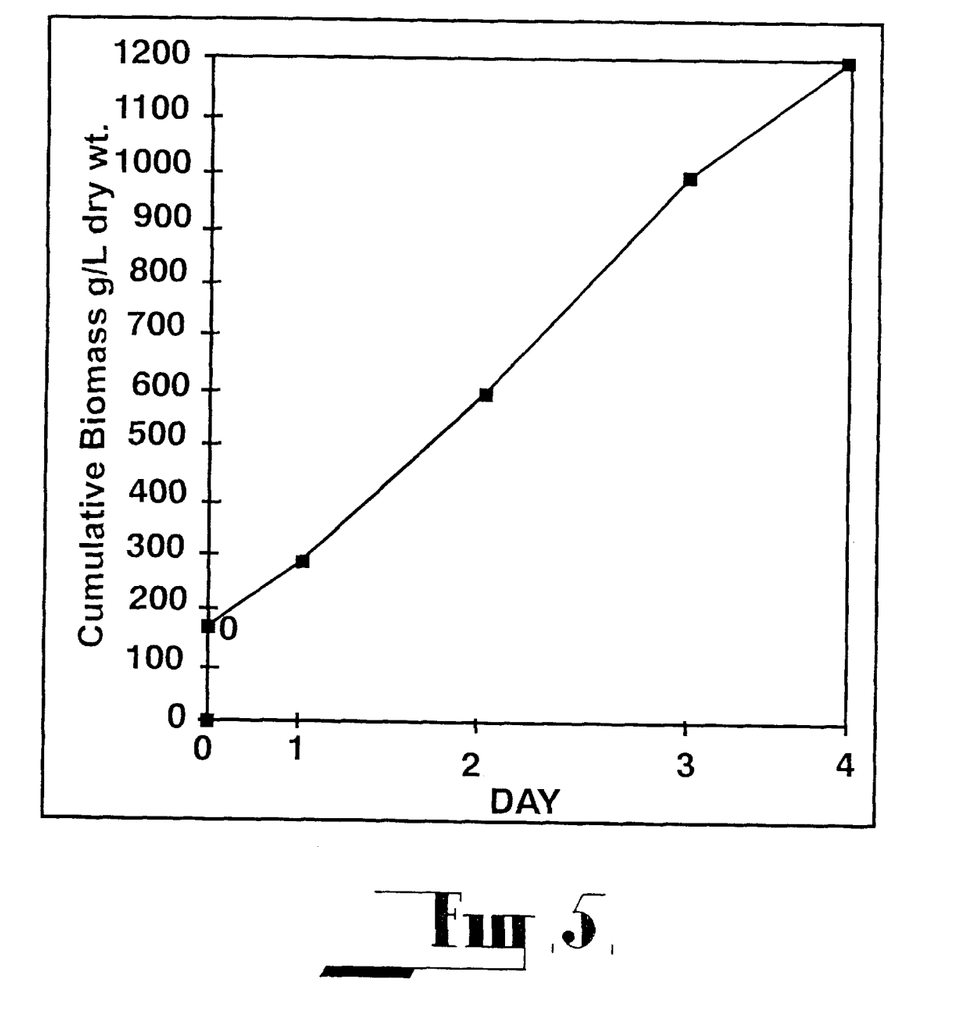
FIG. 5 is a graph of biomass v's time obtained using averaged results from two separate bioreactors of similar form to the bioreactor of FIG. 1, the bioreactors each having a capacity of 450 litres, with triangular dimension of 600 mm and total length of 3000 mm.

FIG. 5 shows biomass increase over time in the 450 litre capacity bioreactor with a triangular cross section of side length 600 mm and which is 3 meters long. The 450 litre bioreactor yielded 1200 mg of biomass per litre in four days under natural daylight conditions.

Figure 6:
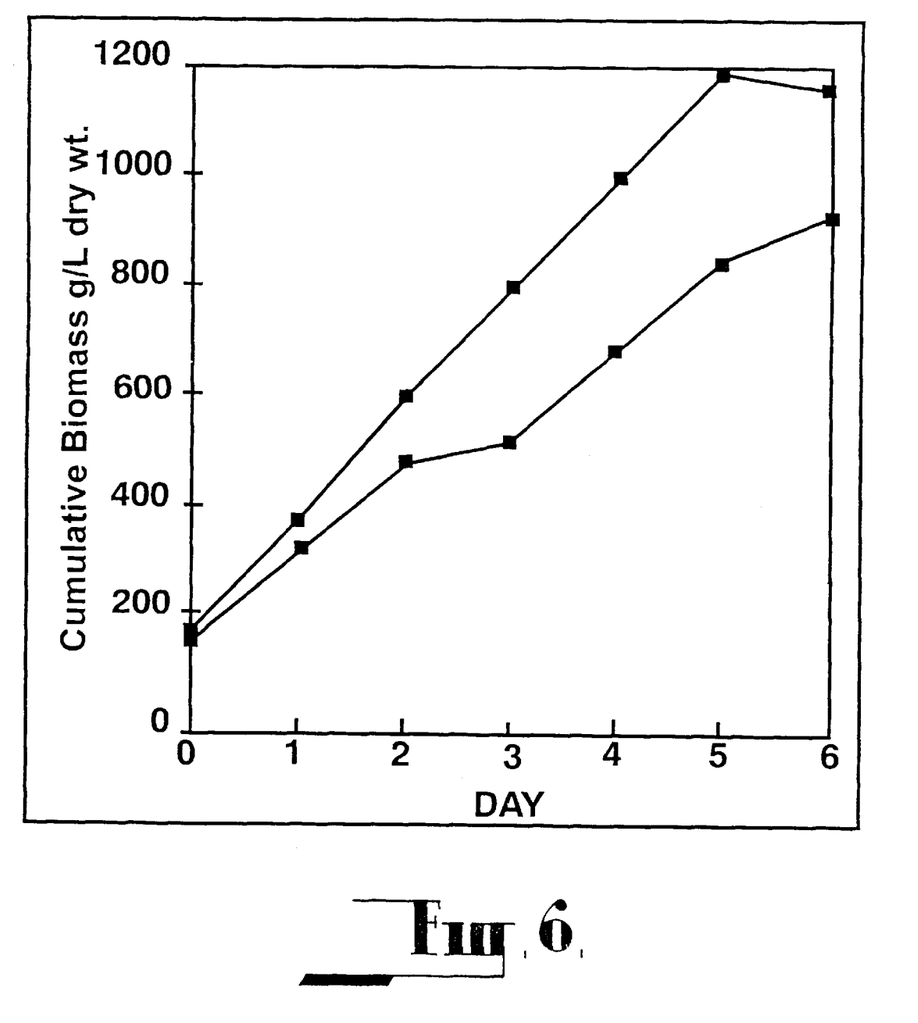
FIG. 6 is a graph of biomass v's time obtained using two separate bioreactors of similar form to the bioreactor of FIG. 1, the bioreactor #1 having a capacity of 350 litres.

FIG. 6 shows biomass increase over time in a 350 litre capacity bioreactor with a triangular cross section of side length 900 mm and which is 1 meter long. The 350 litre bioreactor yielded approximately 1000–1200 mg of biomass per litre in about 6 days under natural daylight conditions.

Figure 7:
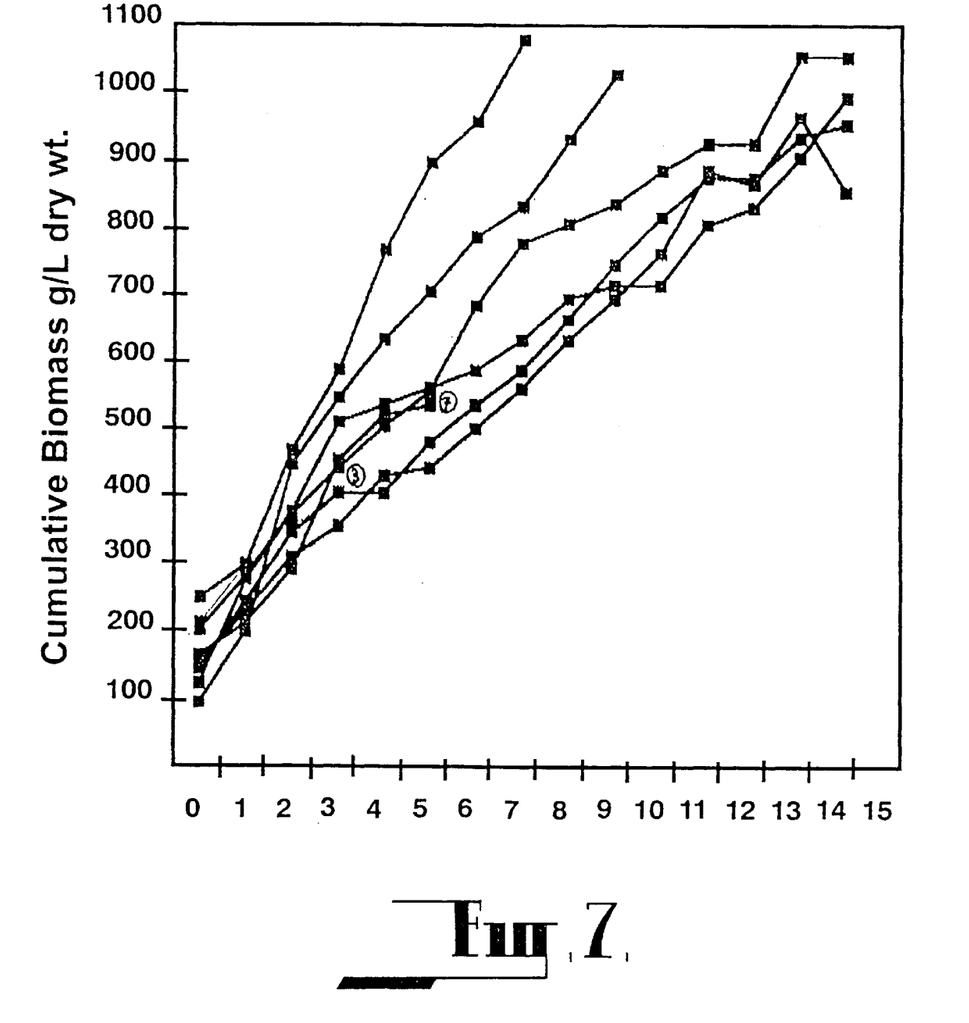
FIG. 7 is a graph of biomass v's time obtained using a bioreactor of similar form to the bioreactor of FIG. 1, with the bioreactors each having a capacity of 3500 litres, a triangular dimension of 900 mm and a length of 10 m. Graph shows curves for eight separate runs. Run 1 depicts a run conducted on 29 Sep. 1995. Run 2 depicts a run conducted on 14 Jun 1995. Run 3 depicts a run conducted on 29 Jun. 1995. Run 4 depicts a run conducted on 14 Jul. 1995. Run 5 depicts a run conducted on 4 Aug. 1995. Run 6 depicts a run conducted on 1 Sep. 1995. Run 7 depicts a run conducted on 2 Nov. 1995. Run 8 depicts a run conducted on 17 Nov. 1995.

FIG. 7 shows biomass increase over time in a 3500 litre capacity bioreactor with a triangular cross section of side length 900 mm and which is 10 meters long. The 3500 litre bioreactor yielded approximately 1100 mg of biomass per litre in about 14–15 days under natural daylight conditions. Yeilds for this vessel average at 63 mg/L/day in winter (over four months). The summer months yielded averages at 120 mg/L/day. This is equivalent to 19.85 gm/day or 11.95 tonnes/hectare for four winter months and 37.8 gm/day or 45.53 tonnes/hectare for eight summer months. These figures are calculated for a triangular tank of 900 mm dimension having a volume of 350 l/m and with the vessel arrangement as described previously, with vessel arranged in parallel rows 1800 mm apart from base apex to base apex. This arrangement results in a total theoretical volume of 1925 $m^3$ per hectare.

It will be appreciated that the invention lends itself to automatic control in particularly by way of computer. Further, by connecting in series the bioreactor embodied by FIG. 1 to 3 it is possible to create a continuous production cycle for the generation of large amounts of biomass.

It will be appreciated that there will be further variations which will be apparent to those skilled in the art from the teaching of the above, such variations are deemed to be within the scope of the invention herein disclosed.

I claim:

1. A bioreactor for biomass production comprising:
   (i) a substantially transparent chamber, the chamber being at least suitable for containing biomass in a liquid phase, and having a base portion, an upper portion and a number of side walls between the base portion and the upper portion, the side walls being configured so as to generally diverge from the base portion towards the wider upper portion; and
   (ii) a circulating means for circulating the contents of the chamber, wherein the circulating means creates a motive force within the liquid phase sufficient to ensure continual mixing of substantially all of the biomass and at least cyclical exposure of biomass to a light source.

2. A bioreactor according to claim 1 wherein the circulation rate within the chamber is at least slightly greater than a circulation rate that would lead to settling of the biomass within the bioreactor.

3. A bioreactor according to claim 1 wherein the circulating means is located within the bioreactor at or near the base portion.

4. A bioreactor according to claim 1 wherein the circulation means is a conduit extending through the length of the chamber which is located near the base portion of the chamber, said conduit being perforated and connected to a gas source such that in operation the passage of gas out of the conduit and into the chamber causes circulation of the chamber contents.

5. A bioreactor according to claim 1 in combination with a reflective base surface, said bioreactor being positioned above said surface.

6. A bioreactor for biomass production comprising:
   (i) a substantially transparent chamber, the chamber being at least suitable for containing biomass in a liquid phase, and having a narrow base portion, an upper portion capable of being sealed by a cover means and a number of side walls diverging from the base portion to the wider upper portion; and
   (ii) a circulation means for circulating the contents of the chamber, wherein the circulating means creates a motive force sufficient to ensure continual mixing of the liquid phase and exposure of biomass to the light wherein the circulating means is located at or near the lower most portion of the base portion and comprises a conduit extending through the length of the bioreactor, the conduit being perforated and connected to a gas source wherein the perforations in the conduit are disposed towards the underside of the conduit, such that in operation the downward passage of gas out of the conduit and into the liquid phase (a) prevents particulate material in the chamber from settling below the conduit, (b) causes circulation of the liquid phase; and (c) allows gas diffusion into the liquid phase.

7. A bioreactor according to claims 1 or 6 wherein the bioreactor chamber is an elongate trough-like prism, the prism having an inverted triangular cross-section, which can accommodate large volumes of liquid phase.

8. A bioreactor according claims 1 or 6 wherein the bioreactor includes a temperature control means for controlling the temperature of the liquid phases.

9. A bioreactor according to claims 1 or 6 wherein the bioreactor contains at least a baffle which is positioned in a fashion to further enhance the circulation of the contents of the chamber.

10. A bioreactor according to claims 1 or 6 wherein the bioreactor includes a pH control means for controlling the pH of the liquid phase.

11. A bioreactor according to claims 1 or 6 wherein the bioreactor comprises one or more light conduction means which promote effective distribution of light within the chamber.

12. A bioreactor according to claims 1 or 6 wherein that bioreactor contains one or more measuring means which are capable of detecting variations in nutrient levels.

13. A bioreactor according to claim 12 wherein the measuring means are connected to a computer control means which is capable of monitoring nutrient levels in the liquid phase and when necessary capable of introducing nutrients into the bioreactor chamber.

14. A bioreactor according to claims 1 or 6 wherein the bioreactor includes one or more jacketing means which are capable of at least partially covering the external surface of the bioreactor.

15. A bioreactor according to claims 1 or 6 wherein the bioreactor is in fluid communication with a separate vessel through which the liquid phase is diverted prior to its return to the bioreactor.

16. A bioreactor according to claim 15 wherein the separate vessel is a reservoir, increasing the volume of the system.

17. A bioreactor according to claim 15 wherein the separate vessel is a dark phase area which is used during high light intensities and growth conditions.

18. A bioreactor according to claim 15 wherein the separate vessel is a settling system from which biomass may be removed from the liquid phase.

19. A bioreactor according to claim 1 or 6, further comprising a means for controlling the internal physical and chemical environment of the bioreactor by one or more computer means which are able to introduce nutrients or chemicals or modify the light or temperature regime of the liquid phase in response to change in one or more of these conditions.

20. A bioreactor according to claims 1 or 6 wherein the liquid phase is pumped through a separate vessel containing an entrained bubble contactor, or other means for dissolving carbon dioxide or other gases into the liquid phase before being returning it to the bioreactor.

21. A bioreactor according to claim 23 wherein the liquid phase is also pumped through a vessel containing a temperature controlling means which is capable of varying the temperature in the liquid phase before being returned to the bioreactor.

22. A bioreactor according to claims 1 or 6 wherein the bioreactor includes a multiple of chambers all of which are interconnected.

23. A bioreactor according to claim 22 wherein one or more of the chambers are cloaked in darkness to aid propagation of the biomass.

24. A bioreactor according to claim 22 wherein the flow of the liquid phase between the chambers is controlled by a computer control means which is capable of monitoring the biomass density within each chamber and which is capable of transferring liquid phase between the chambers in response to changes in biomass density in each chamber.

25. A method of cultivating biomass comprising the step of cultivating biomass in a bioreactor according to claim 1 wherein that biomass is grown in a continuous production cycle wherein there is a steady feed of essential nutrients and liquid phase into the bioreactor as well as a continuous discharge of liquid phase containing cultured biomass from the bioreactor.

26. A bioreactor according to claim 1 or 6, further comprising a cover means sealed to the side walls.

27. A bioreactor according to claim 26, wherein the middle portion of the cover means is elevated relative to the junction between the cover means and the side walls.

28. A bioreactor according to claim 26 wherein the cover means is of an arcuate shape, with a generally angular upper surface.

29. A bioreactor according to claim 28, wherein the upper surface of the cover means is provided with one or more vents positioned towards the middle of the angular upper surface, which enables gas to be vented from the chamber, wherein the liquid phase within the bioreactor is maintained at a level which ensures contact of the liquid phase with the cover means.

30. A bioreactor according to claims 1,2,26,27,28, or 5, wherein the circulating means is located adjacent to the base portion within the bioreactor and is capable of generating an upward movement of biomass and liquid phase from the base portion to the top of the bioreactor whereupon the biomass impacts the top surface of the vessel allowing exposure to external light which may continue as the biomass then moves outwardly towards the sides of the bioreactor and then down the sides of the bioreactor towards the base portion, from where it is again caught by the circulation means and driven upwards towards the top of the bioreactor.

31. A bioreactor according to claim 29 wherein the vents contain a filter means which is capable of preventing particulate from entering the chamber.

\* \* \* \* \*